United States Patent [19]
Wang et al.

[11] Patent Number: 5,100,742
[45] Date of Patent: Mar. 31, 1992

[54] METHOD AND DEVICE FOR GASEOUS FUEL CELL OPERATION

[75] Inventors: Da Y. Wang, Lexington; Daniel T. Kennedy, Burlington, both of Mass.; Burton W. MacAllister, Jr., Hudson, N.H.

[73] Assignee: GTE Laboratories Incorporated, Waltham, Mass.

[21] Appl. No.: 490,812

[22] Filed: Mar. 8, 1990

[51] Int. Cl.⁵ .............................................. H01M 8/10
[52] U.S. Cl. ..................................... 429/13; 429/33; 429/34
[58] Field of Search ....................... 429/13, 30, 33, 34, 429/38, 39; 204/410-412

[56] References Cited

U.S. PATENT DOCUMENTS

| | | | |
|---|---|---|---|
| 4,476,198 | 10/1984 | Ackerman et al. | 429/32 |
| 4,791,035 | 12/1988 | Reichner | 429/31 |
| 4,871,627 | 10/1989 | Strong et al. | 429/34 X |
| 4,883,497 | 11/1989 | Claar et al. | 429/33 X |

Primary Examiner—Anthony Skapars
Attorney, Agent, or Firm—Carl F. Ruoff

[57] ABSTRACT

A fuel cell which converts chemical energy from a fuel/oxidant gas mixture to electricity for power usage or gas-sensing applications is disclosed. The fuel cell has a solid electrolyte wall with electrodes on each side. Each side of the wall is surrounded by a partition which forms a first and second chamber whereon the fuel/oxidant gas mixture is allowed to diffuse. Means are provided to initiate a voltage drop between the electrodes which initiates the chemical reaction. Electricity is collected from the electrodes. In an alternate design the fuel cell has a first and second electrolyte wall with electrodes on each side of the walls. A partition wall separates the first and second walls thereby forming a first chamber with the first wall and the partition wall and a second chamber with the partition wall and the second wall. Gas-flow limiting means exist between the fuel/oxidant gas mixture and the first chamber and the first chamber and the second chamber. The chemical reaction starts spontaneously and electricity is collected and stored from each set of electrodes.

22 Claims, 5 Drawing Sheets

☒ PLATINUM ELECTRODE
☐ YTTRIA STABILIZED ZIRCONIA

PLATINUM ELECTRODE
YTTRIA STABILIZED ZIRCONIA

☒ PLATINUM ELECTRODE
▨ 4% YTTRIA STABILIZED ZIRCONIA
☐ 6-8% YTTRIA STABILIZED ZIRCONIA

METHOD AND DEVICE FOR GASEOUS FUEL CELL OPERATION

BACKGROUND OF THE INVENTION

The present invention relates to a method and apparatus for converting chemical energy to electrical energy for power usage or gas-sensing applications. More specifically, the present invention describes a fuel cell that uses a single gas mixture, such as methane and air, to achieve the spontaneous conversion of chemical energy into electrical energy.

A fuel cell is an electrochemical device that continuously converts the chemical energy of a fuel, such as methane, and an oxidant, such as molecular oxygen, to electrical energy. The fuel and oxidant are continuously supplied to the fuel cell from an external source. The fuel and oxidant are supplied to chambers of the fuel cell which are separated by an electrolyte barrier. This electrolyte barrier can be liquid or molten electrolyte, however, the present invention is concerned with solid electrolytes.

Since fuel cells produce power by an electrochemical reaction rather than a thermal process, they are not subject to the Carnot cycle limitation of combustion engines. This allows for a highly efficient conversion of chemical energy to electric energy. In addition, fuel cells are very clean and quiet in operation as there are no moving parts and the by products from the cell operation are carbon dioxide and water. Furthermore, it is possible to recover the waste heat generated from a fuel cell producing even greater efficiencies.

A conventional solid-state electrolyte fuel cell uses solid non-porous metal oxide electrolyte, such as zirconium oxide as the electrolyte material. With this type of electrolyte, ionic conductivity takes place by the migration of oxygen ions through the lattice of the crystal. Typically, these zirconia cells are operated at elevated temperatures (e.g. 900°C.-1000° C.). Inside the conventional fuel cell the fuel and oxidation gas are required to be separated from each other by the non-porous solid electrolyte which needs two separate sets of gaseous operation equipment. The present invention solves these problems in a unique and novel manner.

SUMMARY OF THE INVENTION

The present invention discloses a method and apparatus for generating electricity from a fuel/oxidant gas mixture for power usage or gas-sensing applications. In one aspect of the invention a fuel cell is provided which has a first solid electrolyte wall in contact with and interposed between a first electrode and a second electrode, a second solid electrolyte partition which forms a first chamber with the first solid electrolyte wall, a third solid electrolyte partition which forms a second chamber with the first solid electrolyte wall, a first gas-flow limiting means between a fuel mixture and the first chamber, a second gas-flow limiting means between the fuel mixture and the second chamber. The gas-flow limiting means can be a physical aperture or a porosity-controlled material which covers the electrode and replaces the space of the gas chamber. The chemical oxidation reaction is initiated by an electrical pulse applied to the first and second electrodes. Afterward, electricity is continuously collected at the first and second electrodes. The chemical oxidation reaction can happen spontaneously if the two gas-flow limiting means are quite different in controlling the respective rates of the gas flow.

In an alternate aspect the fuel cell is provided with a first solid electrolyte wall in contact with and interposed between a first and a second electrode, a second solid electrolyte wall in contact with and interposed between a third and a fourth electrode, a partition wall interposed between the first and third electrodes which creates a first chamber and a second chamber, the first chamber formed by the first electrolyte wall and the partition wall and the second chamber formed by the second electrolyte wall and the partition wall. The fuel cell has a first gas-flow limiting means between the fuel/oxidant gas mixture and the first chamber and a second gas-flow limiting means between the first chamber and the second chamber positioned on the partition wall. The gas-flow limiting means can be a physical aperture or a porosity-controlled material to replace the space occupied by the gas chamber. The chemical reaction starts spontaneously if the temperature and fuel/oxidant gas mixture are within predetermined values. Electricity is collected and stored by means attached to the first and second electrodes or to the third and fourth electrodes.

DETAILED DESCRIPTION OF THE PREFERRED EMBODIMENT

Figure 1:
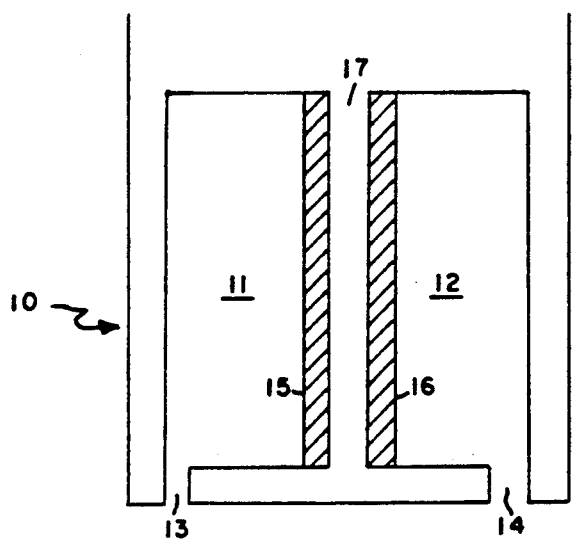
FIG. 1 shows a perspective view of an embodiment of the present invention.

A preferred embodiment of the present invention is shown in detail on FIG. 1. FIG. 1 shows a fuel cell 10 having two partially enclosed chambers 11, 12 where the fuel gas mixture (e.g. methane/air) can enter through orifices 13 and 14. Platinum electrodes 15, 16 are screen printed on both sides of inner wall 17. In a preferred embodiment, inner wall 17 is made of yttria stabilized zirconia, although other oxide anion conducting solid electrolytes are possible such as Mg or Ca stabilized zircon or aliovalent doped ceria and stabilized bismuth oxide. Although orifices 13, 14 are used for limiting the gas-flow, other means are possible, such as using gas permeable (porosity-controlled) material to replace the gas chambers. The porosity-controlled material can be solid materials such as $SiO_2$, $Al_2O_3$ or the same electrolyte material used in the electrolyte walls.

In order to operate the present invention, fuel cell 10 is exposed to a fuel gas/oxidant mixture. The device is heated to a temperature sufficient to raise the electrical conductivity of the zirconia to a predetermined level. The fuel cell operation is initiated by applying a pulse of voltage to the platinum electrodes 15, 16. The magnitude of the voltage pulse decreases with increasing temperature. At high temperature (approximately 400° C.) the initiating pulse can be several mV and at low temperature (approximately 250° C.) the pulse can be several thousand mV. This electrical stimulation can be eliminated if the degrees of gas-flow limitation are different between the two electrodes. The electrical stimulation can also be eliminated by using two metals which have different electrochemical exchange rates for the two electrodes (e.g. An Au electrode versus Pt electrode).

Figure 2:
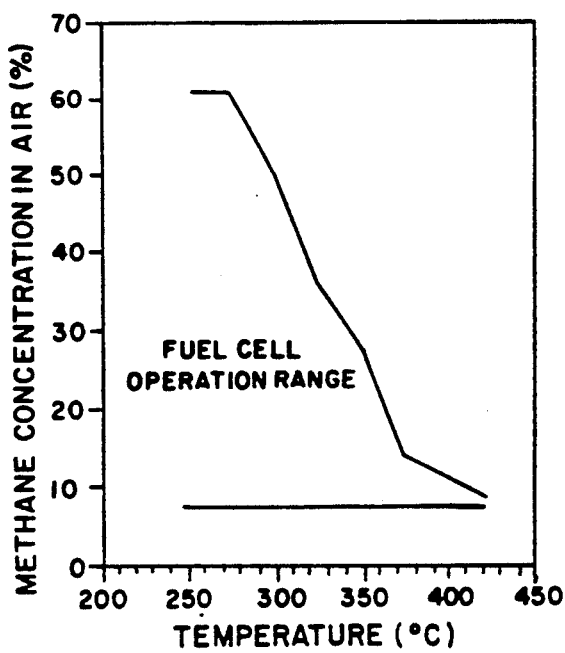
FIG. 2 shows the temperature and gas mixture ranges for methane/air required for fuel cell operation of the device shown in FIG. 1.

There is a range for both temperature and fuel concentration for which the device of FIG. 1 operates as a fuel cell. Shown in FIG. 2 is the concentration range and temperature range for which the device in FIG. 1 operates as a fuel cell using a methane/air gas mixture. This diagram clearly shows that for a temperature greater than 450° C. or a methane concentration in air of less than 7.3%, the device shown in FIG. 1 will not operate as a fuel cell.

Figure 3:
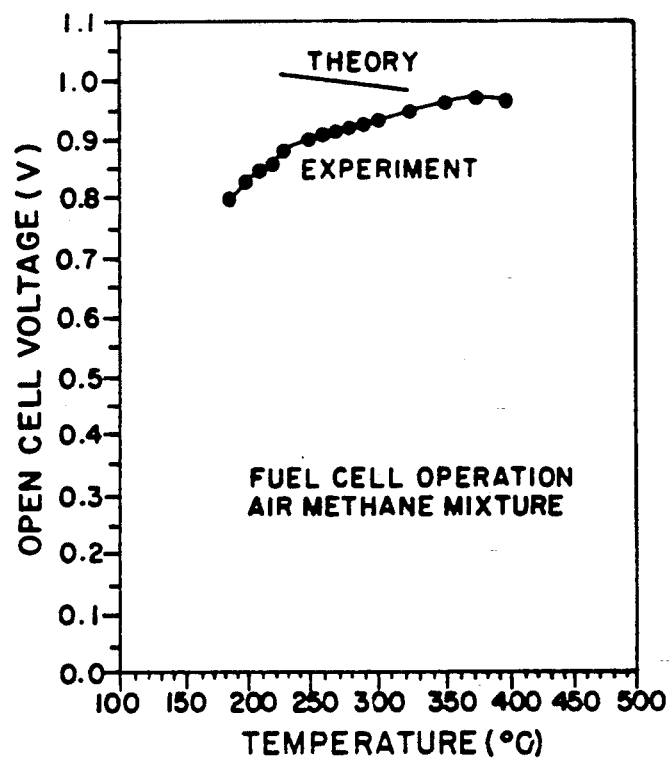
FIG. 3 shows a comparison of theoretical EMF versus actual EMF for a methane/air mixture for various temperatures.

A comparison of the open cell EMF (electromotive force or voltage) obtained from the device shown in FIG. 1 versus the theoretical EMF (thermodynamic value) is shown in FIG. 3.

FIG. 3 shows that at higher temperatures (>350° C.) the theoretical and actual open cell EMF are almost identical. At low temperatures, the discrepancy between actual EMF and theoretical EMF may be caused by the high internal resistance created by the slow electrodes reactions.

Figure 4:
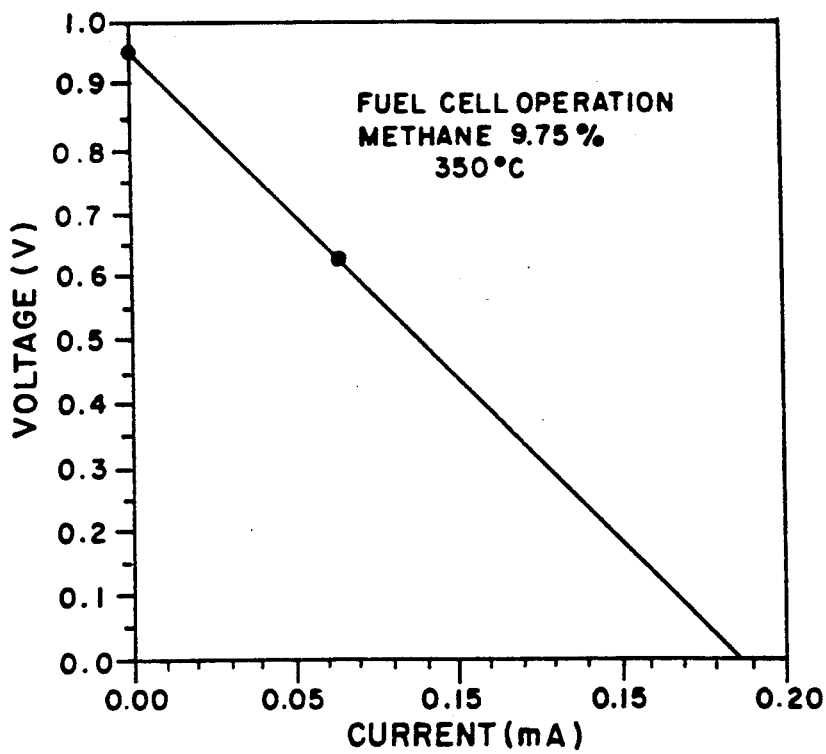
FIG. 4 shows the load line plot of the fuel cell of FIG. 1 operated with a 9.75% methane in air mixture at 350° C.
Figure 5:
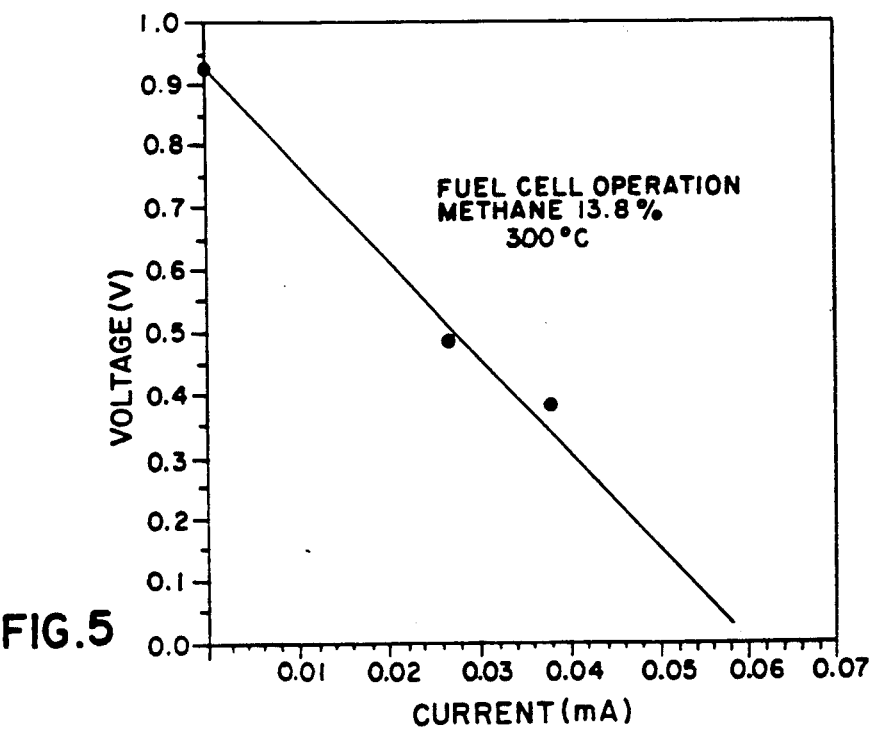
FIG. 5 shows the load line plot of the fuel cell of FIG. 1 operated with a 13.8% methane in air mixture at 300° C.

Shown in FIGS. 4 and 5 are current versus voltage plots of the fuel cell of FIG. 1 in operation. FIG. 4 shows a 9.75% methane in air fuel mixture at 350° C. The power obtainable from the fuel cell is the current multiplied by the voltage. A similar diagram is shown in FIG. 5 for a 13.8% methane in air fuel mixture with the device operated at 300° C.

Figure 6:
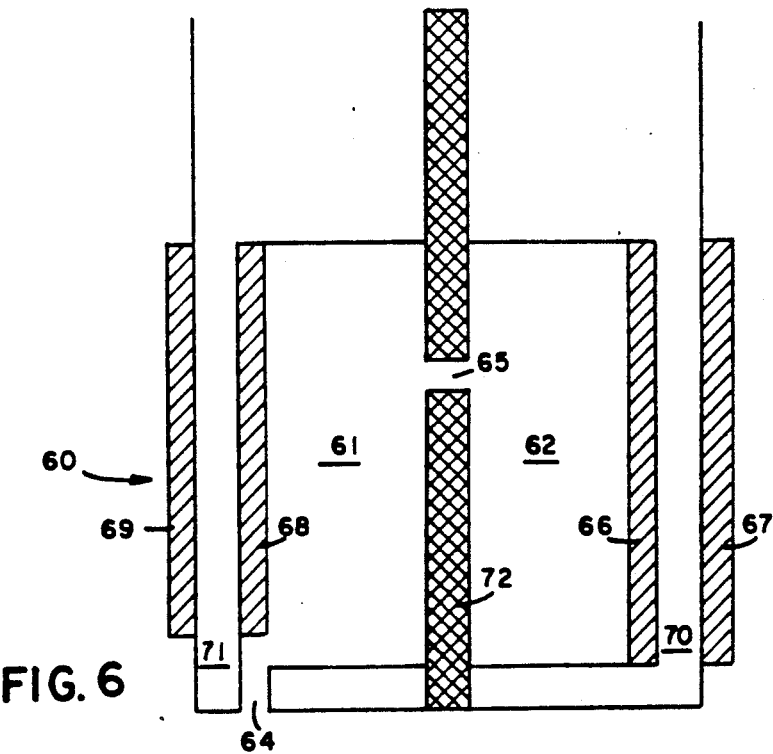
FIG. 6 shows a perspective view of an alternate embodiment of the present invention.

Although, only methane mixture is used here, the fuel type is not limited so. It can be any reducing gas such as $H_2$, CO, alkanes or alkenes. An alternate embodiment of the fuel cell of the present invention is shown in FIG. 6. FIG. 6 shows a fuel cell 60 which contains two partially enclosed chambers, an inner cell 62 and an outer cell 61. The fuel mixture (fuel/air or fuel/oxygen) enters the outer cell 61 through first orifice 64 and the inner cell through second orifice 65. Other means for gas-flow limiting control can be used such as gas permeable porosity-controlled solid material to replace the gas chambers. The porosity-controlled materials can be $Al_2$, $SiO_2$ or the same electrolyte material used in the electrolyte walls. The electrodes 66, 67, 68, 69 are screen printed on both sides of the two walls 70 and 71 which separate the cells 61 and 62 from the ambient fuel mixture. In a preferred embodiment the electrodes 66, 67, 68, 69 are platinum, however, other electrical conducting material may be used and different electrode materials can be used in the same fuel cell. Examples of possible electrode material include platinum, silver, nickel, titanium, gold and palladium and mixtures thereof. The four electrodes 66, 67, 68, 69 are used to draw current or monitor voltage developed by operation of the fuel cell 60. Partition wall 72 separates the inner cell 62 and the outer cell 61.

In the tests run on the fuel cell 60, the walls 70 and 71 are made of 6–8% yttria stabilized zirconia although any other electrolyte material which conduct oxygens ions such as yttria doped ceria can be used. The partition wall 72 separating the inner and outer cells 62, 61 can be any material. In the present case the partition wall was made of 4% yttria stabilized zirconia.

Figure 7:
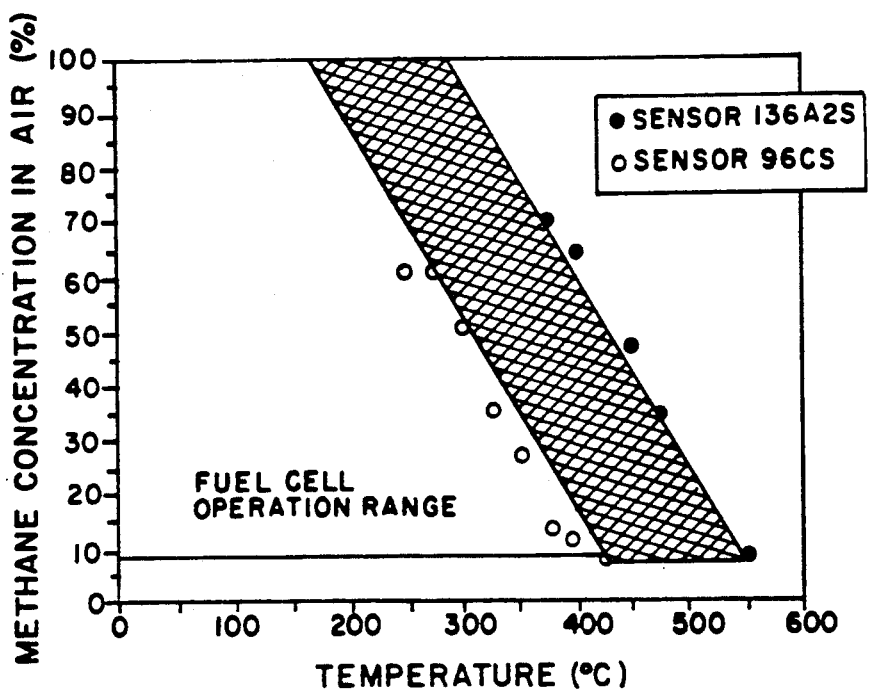
FIG. 7 shows a comparison between the fuel cell of FIG. 1 and the fuel cell of FIG. 6 for temperature and gas mixture ranges of methane/air required for fuel cell operation.

Substantial improvements in results are obtained from using the device in FIG. 6 than the device in FIG. 1. Initially the device is heated to a temperature where the solid zirconia electrolyte has a predetermined ionic conductivity. Shown in FIG. 7 is the improvement in operating conditions from the fuel cell in FIG. 6 over the fuel cell in FIG. 1. With the fuel cell in FIG. 6 it is possible to operate at temperatures approaching 600° C. and the methane concentration in air can be as low as 7.3%.

Figure 8:
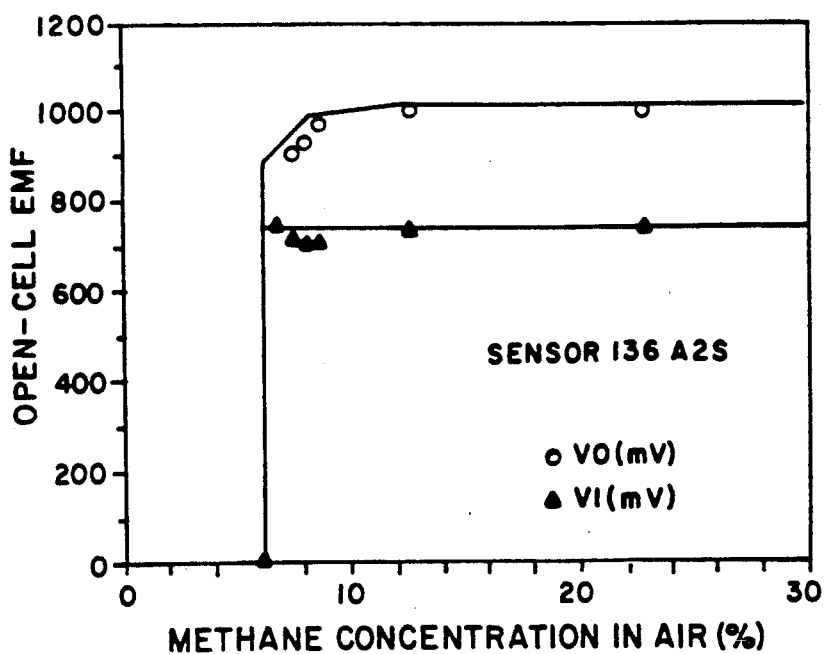
FIG. 8 shows a plot of open cell EMF for the inner and outer cells of the device in FIG. 6 versus methane concentration in air at 425° C.

FIG. 8 presents open cell EMF measured versus methane concentration in air at 425° C. from the inner and outer cells of the fuel cell of FIG. 6. FIG. 8 shows that the inner cell 62 operates at a lower EMF than the outer cell 61.

Figure 9:
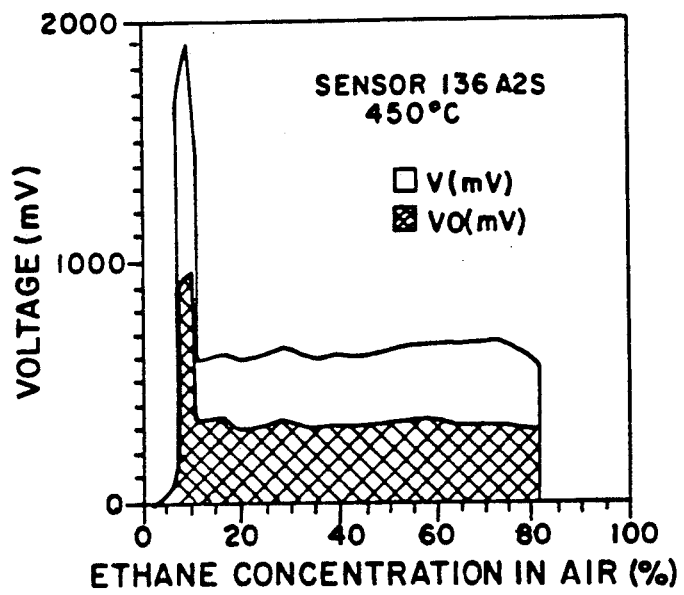
FIG. 9 shows a plot of the open cell EMF for the inner and outer cells of FIG. 6 versus ethane concentration in air at 450° C.
Figure 10:
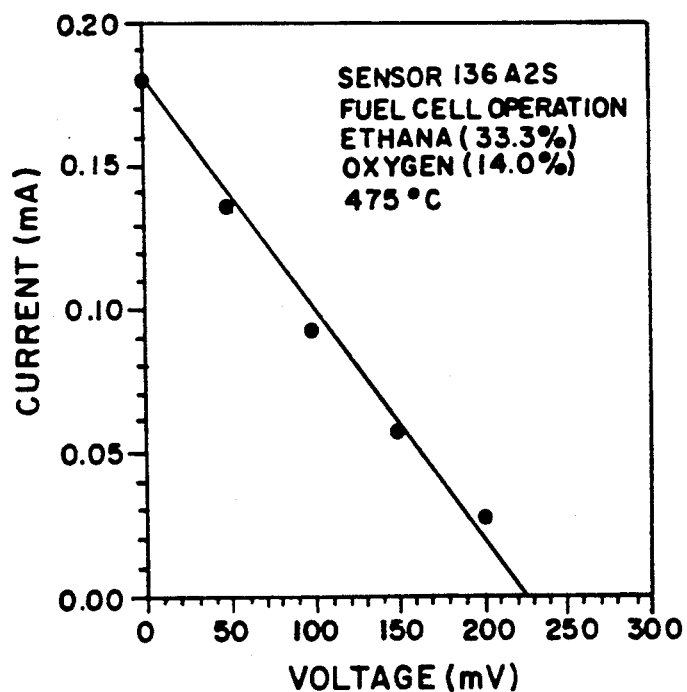
FIG. 10 shows the load line plot for the outer cell of FIG. 6 using a 33% ethane in air gas mixture at 475° C.

An ethane gas/air fuel mixture was used in the cell of FIG. 6 and the results are shown in FIG. 9 and 10. FIG. 9 shows the open cell EMF for the inner and outer cells versus ethane concentration in air at 450° C. For clarity of the figures, the inner cell results are plotted on top of the outer cell's results. As shown in FIG. 9, both cells give similar EMF outputs. FIG. 10 shows the load line plot of the outer cell for a 33% ethane in air fuel mixture operated at 475° C. FIG. 9 and 10 show that it is possible to use other fuels than methane.

An important feature of the cell of FIG. 6 is that there is no requirement that an initial pulse be used to initiate fuel cell operation because the big difference in gas-flow rates between the first and second electrodes and the third and fourth electrodes. In addition, the fuel cell operating temperature and concentration requirements are extended. Both the embodiments shown in FIG. 1 and FIG. 6 do away with the need for separating the fuel and the oxidant to operate the cell.

The power or the gas-sensing electricity will be collected between the first and second electrodes, or the third and fourth electrodes. The electricity can be utilized to drive electronic circuits in a remote area or to power an alarming circuit for gas leakage detection.

While the present invention has been described, the preferred embodiment thereof, various alterations, modifications and changes may be made by those skilled in the art without departing from the scope and spirit of the invention. All such alterations are intended to be covered by the appended claims.

What is claimed is:

1. A fuel cell for generating electricity or gas-sensing in a fuel-oxidant gas mixture comprising a first solid electrolyte wall in contact with and interposed between a first electrode and a second electrode;

a second solid electrolyte partition which forms a first chamber with said first solid electrolyte wall;

a third solid electrolyte partition which forms a second chamber with said first solid electrolyte wall;

a first gas-flow limiting means between a fuel mixture and said first chamber;

a second gas-flow limiting means between the fuel mixture and said second chamber; and a fuel-oxidant gas mixture to which the first electrodes and the second electrodes are exposed; and means to collect and store energy generated from the electrochemical reaction between the first and the second electrodes.

2. The fuel cell of claim 1 wherein said first solid electrolyte wall is made of an oxide electrolyte.

3. The fuel cell of claim 2 wherein in the oxide electrolyte comprises yttria or calcia stabilized zirconia.

4. The fuel cell of claim 1 wherein said first and said second gas-flow limiting means comprise a porosity-controlled solid material.

5. The fuel cell of claim 4 wherein the porosity-controlled solid material is made of alumina or silica.

6. The fuel cell of claim 1 wherein the fuel oxidant mixture comprises at least 8.75% methane in air.

7. The fuel cell of claim 1 wherein said first and said second electrodes are selected from the group consisting of platinum, silver, nickel, titanium, gold, and palladium and mixtures thereof.

8. The fuel cell of claim 1 further comprising means to initiate an electrochemical reaction in the fuel mixture, said means connected to said first and second electrodes.

9. A fuel cell for generating electricity in a fuel/oxidant gas mixture comprising a first solid electrolyte wall in contact with and interposed between a first and a second electrode;

a second solid electrolyte wall in contact with and interposed between a third and a fourth electrode;

a partition wall interposed between said first and third electrodes which creates a first chamber and a second chamber, said first chamber formed by said first electrolyte wall and said partition wall and said second chamber formed by said second electrolyte wall and said partition wall;

a first gas-flow limiting means between the fuel/oxidant gas mixture and said first chamber;

a second gas-flow limiting means between said first chamber and said second chamber position on said partition wall; and means for collecting and storing energy from the first and second electrodes or the third and fourth electrodes;

wherein an electrochemical reaction spontaneously occurs between the fuel/oxidant gas mixture.

10. The fuel cell of claim 9 wherein said first and second electrolyte wall are made of an oxide electrolyte.

11. The fuel cell of claim 10 wherein the oxide electrolyte comprises yttria or calcia stabilized zirconia.

12. The fuel cell of claim 9 wherein said first and said second gas-flow limiting means comprises a porosity-controlled solid material.

13. The fuel cell of claim 12 wherein the porosity-controlled solid material is made of alumina or silica.

14. The fuel cell of claim 9 wherein said partition wall is made of yttria or calcia partially stabilized zirconia.

15. The fuel cell of claim 9 wherein the fuel/oxidant mixture comprises at least 8.75% methane in air.

16. The fuel cell according to claim 9 wherein said first, second, third, and fourth electrodes are selected from the group consisting of platinum, silver, nickel, titanium, palladium and mixtures thereof.

17. A method of generating electricity from a fuel/oxidant gas mixture or sensing gas of a fuel/oxidant gas mixture comprising:

providing a fuel cell having a first solid electrolyte wall in contact with and interposed between a first electrode and a second electrode and a second solid electrolyte wall in contact with and interposed between a third electrode and a fourth electrode, said second and fourth electrodes in communication with the fuel/oxidant gas mixture, a partition wall interposed between said first and third electrodes which creates a first chamber and a second chamber, said fuel cell having a first gas flow limiting means between the fuel/oxidant gas mixture and the first chamber and a second gas flow limiting means between the first chamber and the second chamber;

collecting and storing electricity generated from said first and second electrodes and from said third and fourth electrodes.

18. The method of claim 17 wherein said first and second electrolyte wall is made of an oxide electrolyte material/zirconia.

19. The method of claim 17 wherein the first and second gas flow limiting means comprises a porosity-controlled material.

20. A method of generating electricity from a fuel/oxidant gas mixture comprising:

providing a fuel cell having a first solid electrolyte wall in contact with and interposed between a first electrode and a second electrode;

a second solid electrolyte partition which forms a first chamber with said first solid electrolyte wall, a third solid electrolyte partition which forms a second chamber with said first electrolyte wall, and fuel cell having a first gas flow limiting means between said first chamber and the fuel/oxidant gas mixture and a second gas flow limiting means between said second chamber and the fuel gas/oxidant mixture;

providing a means to initiate an electrical pulse between said first and second electrodes;

collecting and storing electricity generated from said first and second electrodes.

21. The method according to claim 20 wherein said first electrolyte wall, said second electrolyte partition and said third electrolyte partition are all made of an oxide electrolyte materials.

22. The method according to claim 20 wherein the first and second gas flow limiting means comprises a porosity-controlled material.

* * * * *